(12) United States Patent
Patel et al.

(10) Patent No.: US 7,385,076 B2
(45) Date of Patent: Jun. 10, 2008

(54) PROCESS FOR THE PREPARATION OF PHENYLCARBAMATES

(75) Inventors: Hetalkumar Virendrabhai Patel, Baroda (IN); Rajamannar Thennati, Baroda (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 14 days.

(21) Appl. No.: 10/516,104

(22) PCT Filed: Jun. 2, 2003

(86) PCT No.: PCT/IN03/00210

§ 371 (c)(1),
(2), (4) Date: Aug. 7, 2006

(87) PCT Pub. No.: WO03/101917

PCT Pub. Date: Dec. 11, 2003

(65) Prior Publication Data

US 2006/0293518 A1    Dec. 28, 2006

(30) Foreign Application Priority Data

May 31, 2002   (IN) .................... 484/MUM/2002
Feb. 6, 2003   (IN) .................... 166/MUM/2003

(51) Int. Cl.
*C07C 269/00*    (2006.01)
*C07C 215/00*    (2006.01)

(52) U.S. Cl. ..................... 560/136; 564/503
(58) Field of Classification Search .............. None
See application file for complete search history.

(56) References Cited

FOREIGN PATENT DOCUMENTS

| DE | 3805744 A1 | 9/1988 |
| EP | 0 193 926 B1 | 9/1986 |
| EP | 0 359 647 A1 | 3/1990 |

OTHER PUBLICATIONS

Grazyna Ciszewska et al., J. Label Comps. Radiopharm 1997, 39 (8), pp. 651-668.

Marta Weinstock et al., Pharmacological Activiy of Novel Anticholinesterase Agents of Potential Use in the Treatment of Alzheimer's Disease, pp. 539-549, 2004.

*Primary Examiner*—Paul A Zucker
(74) *Attorney, Agent, or Firm*—Westerman, Hattori, Daniels & Adrian, LLP.

(57) ABSTRACT

A process for the preparation of compound of formula (I); wherein $R^1$ is hydrogen, linear, branched or cyclic lower alkyl, cyclohexyl, allyl, propargyl or benzyl; $R^2$ is hydrogen, methyl, ethyl or propyl; or $R^1$ and $R^2$ together with the nitogen to which they are attached form a cyclic moiety of three to eight-membered ring, with or without a hetero atom like nitrogen or oxygen; $R^3$ is hydrogen or lower alkyl; $R^4$ and $R^5$ are the same or different and each is a lower alkyl; comprising reacting compound of formula (II); wherein $R^3$, $R^4$ and $R^5$ are as defined above, with compound of formula (III); wherein $R^1$ and $R^2$ are as defined above, in the presence of a base, and further resolving the compound of formula (I) to obtain (S)-isomer of compound of formula (I), substantially free of R-isomer

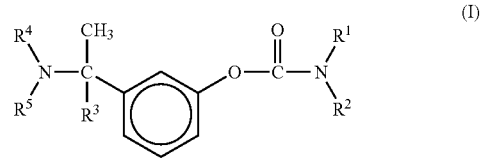

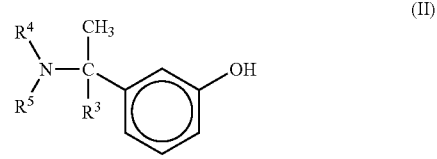

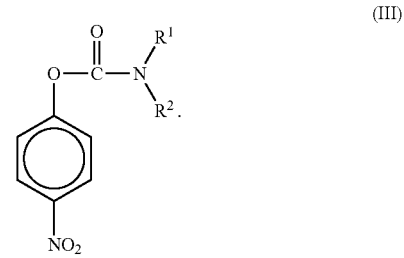

20 Claims, No Drawings

PROCESS FOR THE PREPARATION OF PHENYLCARBAMATES

The present invention relates to a process for the preparation of phenyl carbamates of formula I,

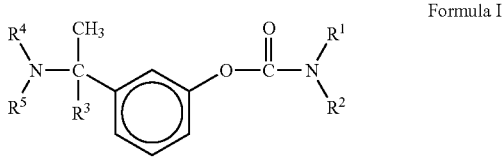

Formula I wherein $R^1$ is hydrogen, linear, branched or cyclic lower alkyl, cyclohexyl, allyl, propargyl or benzyl; $R^2$ is hydrogen, methyl, ethyl or propyl; or $R^1$ and $R^2$ together with the nitrogen to which they are attached form a cyclic moiety of three to eight-membered ring, with or without a hetero atom like nitrogen or oxygen; $R^3$ is hydrogen or lower alkyl; $R^4$ and $R^5$ are the same or different and each is a lower alkyl.

Particularly, the process of the present invention relates to the preparation of ethylmethylcarbamic acid 3-[1-(dimethylamino)ethyl]phenyl ester, commonly known as Rivastigmine (INN name). More particularly, the present invention relates to a process for the preparation of the racemate and the enantiomerically active form of ethylmethylcarbamic acid 3-[1-(dimethylamino)ethyl]phenyl ester.

The present invention also provides a process for the preparation of 1-(3-hydroxyphenyl)alkyl-(N-mono/dialkyl)amine of formula II,

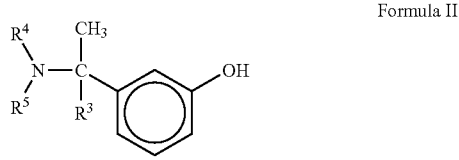

Formula II wherein $R^3$, $R^4$ and $R^5$ are as described above.

BACKGROUND OF THE INVENTION

Prior Art on Compound of Formula I

European Patent 193926 claims phenyl carbamate compounds and their pharmacologically acceptable salts for use as pharmaceutical agents producing anticholinesterase activity in the central nervous system. The patent discloses the process for the preparation of the title phenyl carbamate compounds involving reaction of hydroxyphenyl-substituted alkyl amines with appropriate isocyanates or carbamoyl halides. The process using isocyanates involves the use of benzene as a solvent. Isocyanates such as lower alkyl isocyanates are hazardous to handle due to their toxic and non-volatile nature. The other alternative reported is the use of carbamoyl halides along with reactive bases like sodium hydride, to prepare the carbamates. The carbamoyl halides are not easy to handle at industrial scales and involve safety hazards. The use of a reactive base like sodium hydride on an industrial scale is hazardous and operationally non-user friendly due to its pyrophoric and reactive nature. More importantly, as per the process, 200% excess of the reagent is required for the reaction, and absolutely anhydrous conditions need to be employed. The excess reagent is quenched with water. This process would cause uncontrollable exothermicity at an industrial scale, and it is also possible that the highly alkaline conditions resulting from the formation of sodium hydroxide during the quenching of excess sodium hydride would cause degradation of the product formed, the degradation being more extensive at reaction temperatures above ambient temperature.

The prior art employs reagents like isocyanates and carbamoyl halides to make carbamates and in the process solvents like benzene, in case of isocyanates, or anhydrous reaction conditions with the use of sodium hydride, are necessary to carry out the reaction. Performing these reactions on a large scale entails several safety measures, in terms of storage, handling and quenching excess of reagents, as well as the poor quality of the end product.

The present invention avoids the above mentioned drawbacks by providing a process for the preparation of compound of formula I,

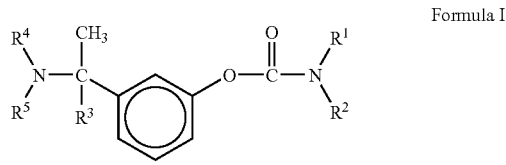

Formula I wherein $R^1$ is hydrogen, linear, branched or cyclic lower alkyl, cyclohexyl, allyl, propargyl or benzyl; $R^2$ is hydrogen, methyl, ethyl or propyl; or $R^1$ and $R^2$ together with the nitrogen to which they are attached form a cyclic moiety of three to eight-membered ring, with or without a hetero atom like nitrogen or oxygen; $R^3$ is hydrogen or lower alkyl; $R^4$ and $R^5$ are the same or different and each is a lower alkyl; comprising reacting compound of formula II,

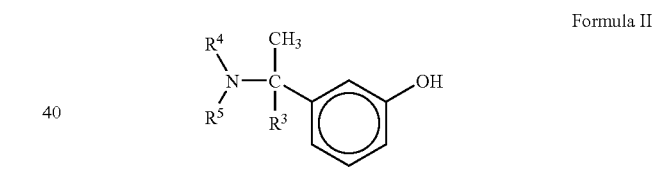

Formula II wherein $R^3$, $R^4$ and $R^5$ are as defined above, with compound of formula III,

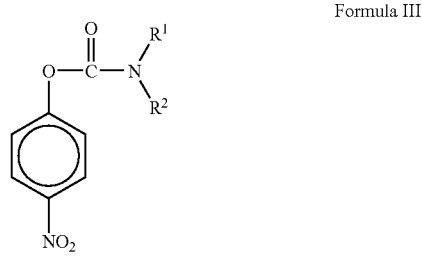

Formula III wherein $R^1$ and $R^2$ are as defined above, in the presence of a base.

Prior Art on Compound of Formula II

The present invention also provides a novel process for the preparation of 1-(3-hydroxyphenyl)alkyl-(N-mono/dialkyl)amine, compound of formula II.

The process for the preparation of 1-(3-hydroxyphenyl)alkyl-(N-mono/dialkyl)amine of formula I from 1-(3-methoxyphenyl)alkyl-(N-mono/dialkyl)amine by demethylation is known in the prior art. For example, J. Labelled Comp. And Radiopharm. 1997, 39(8), 651-668 reports a process involving a final step of demethylation of the methoxy function of 1-(3-methoxyphenyl)ethyl-(N,N-dimethyl) amine, using hydrobromic acid in the presence of hexadecyltributyl phosphonium bromide as the phase transfer catalyst, to yield 1-(3-hydroxyphenyl)ethyl-(N,N-dimethyl) amine. The use of hydrobromic acid, with or without the use of phase transfer catalysts, for demethylation of the methoxy function has a disadvantage in that the quality of the final product is not satisfactory due to a number of impurities formed in the reaction. Also, the process involves the use of expensive reagents such as phase transfer catalysts.

European Patent No. 359647 discloses a process for the preparation of morphinane derivatives involving demethylation of 3-methoxylated compounds using a sulphonic acid chosen from among methanesulphonic acid and trifluoromethanesulphonic acid, in the presence of a sulphide. However, the disadvantage of using sulfonic acid such as methanesulfonic acid is that it is a very expensive reagent and large volumes of the acid are required to isolate the final product.

There exists a need for a process for the preparation of 1-(3-hydroxyphenyl)alkyl-(N-mono/dialkyl)amine, compound of formula II, such that the process utilizes easily available starting materials, simple reagents and standard reaction conditions. The process should result in 1-(3-hydroxyphenyl)alkyl-(N-mono/dialkyl)amines of satisfactory quality, in a satisfactory yield.

OBJECT OF THE INVENTION

The object of the present invention is to provide a novel and safe route for the preparation of compound of formula I. The present invention is materially different in that it uses simple reagents that are easy to handle and store.

Another object of the present invention is to provide S-isomer of the phenyl carbamates.

Yet another object of the invention is to provide a process for the preparation of 1-(3-hydroxyphenyl)alkyl-(N-mono/dialkyl)amine, compound of formula II, wherein readily available starting material such as 1-(3-alkoxyphenyl)alkyl-(N-mono/dialkyl)amine, compound of formula IV, wherein R maybe selected from methyl, ethyl and benzyl, is subjected to dealkylation using simple reagents. The process of the present invention yields the 1-(3-hydroxyphenyl)alkyl-(N-mono/dialkyl)amine, compound of formula II, in a satisfactory quality and quantity.

SUMMARY OF THE INVENTION

The present invention provides a process for the preparation of compound of formula I,

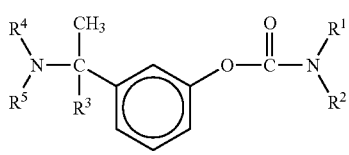

Formula I wherein $R^1$ is hydrogen, linear, branched or cyclic lower alkyl, cyclohexyl, allyl, propargyl or benzyl; $R^2$ is hydrogen, methyl, ethyl or propyl; or $R^1$ and $R^2$ together with the nitrogen to which they are attached form a cyclic moiety of three to eight-membered ring, with or without a hetero atom like nitrogen or oxygen; $R^3$ is hydrogen or lower alkyl; $R^4$ and $R^5$ are the same or different and each is a lower alkyl; comprising reacting compound of formula II,

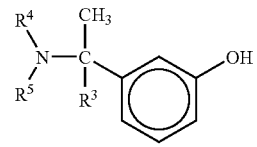

Formula II wherein $R^3$, $R^4$ and $R^5$ are as defined above, with compound of formula III,

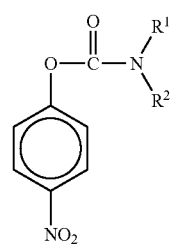

Formula III wherein $R^1$ and $R^2$ are as defined above, in the presence of a base.

The present invention also provides a process for the preparation of compound of formula II,

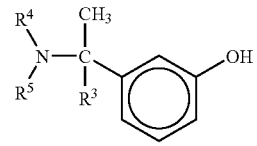

Formula II wherein $R^3$ is hydrogen or lower alkyl; $R^4$ and $R^5$ are the same or different and each is a lower alkyl; comprising dealkylating compound of formula IV,

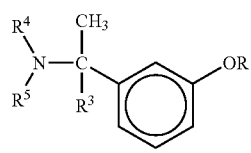

Formula IV wherein R is methyl, ethyl or benzyl and $R^1$, $R^2$ and $R^3$ are as defined above, said dealkylation comprising reaction of compound of formula IV with a mixture of thioether and mineral acid.

DETAILED DESCRIPTION OF THE INVENTION

Preparation of Compound of Formula I

The process of the present invention involves the reaction of compound of formula II with compound of formula III, in the presence of a base. The base used in this reaction is selected from a group comprising of alkali and alkaline earth metal oxides or hydroxides or carbonates, and secondary or tertiary amine bases such as dimethylaminopyridine, N-ethyldiisopropyl amine, collidine and the like. In a preferred embodiment the base used is an alkali or alkaline earth metal carbonate, more preferably potassium carbonate. The mole ratio of base used with respect to compound of formula II, is in the range of about 0.5 moles to about 5 moles, preferably from about 1 mole to 3 moles, more preferably from about 1 to 2 moles.

The process of the present invention can be carried out using an organic solvent(s) having a boiling point greater than 60° C. In preferred embodiments polar protic or aprotic solvents selected from the group comprising amides, ethers, polyethylene glycols (molecular weight 200 to 10,000), sulfoxides, sulphones and the like, are used to carry out the reaction. Preferably, amides and sulfoxides like dimethyl sulfoxide are used as solvents in the process of the present invention.

The process of the present invention may be carried out at a temperature ranging from ambient temperature to about 150° C., preferably from about 50° C. to about 120° C., more preferably from about 80° C. to about 110° C. The reaction mixture is then filtered and quenched to obtain the desired product.

The compound of formula I, may be further purified by methods known to those skilled in the art. The most common techniques being distillation, solvent extraction, chromatography, crystallization, recrystallization etc., preferably by solvent extraction. Solvent extraction may be carried out with a water immiscible solvent selected from a group comprising of a saturated aliphatic hydrocarbon consisting of linear hydrocarbons having about 6 to about 12 carbon atoms viz., hexane, heptane, octane, and the like, a cyclo aliphatic hydrocarbon viz., cyclohexane methylcyclohexane and the like, an aromatic hydrocarbon viz., benzene, biphenyl, naphthalene, toluene, xylene and alkyl derivatives thereof having 1 to 4 carbon atoms, a halogenated hydrocarbon viz., dichloromethane, chloroform perchloroethylene, ethane dichloride, trichloroethane and the like, an ester viz., ethyl acetate, hexyl acetate, ethyl butyl acetate, amyl acetate, benzyl acetate and the like. The preferred being hexane, ethyl acetate, toluene and dichloromethane and the most preferred being ethyl acetate.

In one embodiment, the process of the present invention provides a racemate of compound of formula I.

In a preferred embodiment, the (S)-isomer of ethylmethylcarbamic acid 3-[1-(dimethylamino)ethyl]phenyl ester, compound of formula I, is separated from the racemate of the compound of formula I, by methods such as conversion of the isomers to diastereomeric chiral acid addition salts, separation of these salts by fractional crystallization, and various other procedures known to a person skilled in the art.

Preparation of Compound of Formula II

Compound of formula II, which is used as the starting material for the preparation of compound of formula I, may be obtained by dealkylation of the 1-(3-methoxyphenyl) alkyl-(N-mono/dialkyl)amine using a mixture of thioether and mineral acid.

The thioether may be selected from a group comprising of alkyl sulphides, 3-(methylthio)propionic acid, cycloalkyl methyl sulphides, dicycloalkyl sulphides, diphenyl or substituted diphenyl sulphides, phenyl or substituted phenyl methyl sulphide, dibenzylidene sorbitol-4-thioether, S-carboxymethylcysteine, S-carboxymethyl homocysteine, thiolane-3,4-diol, thiolane-3,4-diol S-oxide, tetrahydrothiophene, dithiane, trithiane, methionine and the like, preferred being methionine The mineral acid may be selected from the group comprising of hydrochloric acid, nitric acid, sulfuric acid and the like, preferably sulfuric acid. The concentration of sulfuric acid that can be used may range from 20% to 100%, preferred being 35% to 70% and most preferred being 50%, which is easier to handle than concentrated sulfuric acid on large scale The dealkylation step is carried out by adding methionine to 1-(3-alkoxyphenyl)alkyl-(N-mono/dialkyl)amine, compound of formula II, in molar ratio ranging from about 0.5:1 to 3.0:1, preferred being 1:1 to 2.5:1 and most preferred being 1.5:1 to 2.0:1.

The process is carried out at a temperature ranging from ambient to about 150° C., preferably about 70° C. to 130° C.; the most preferred being about 110 to 120° C. The reaction takes place at mild to moderate pressure, preferred being atmospheric pressure.

The compound of formula II may be further purified by methods known to those skilled in the art. The most common techniques being distillation, solvent extraction, chromatography, crystallization, recrystallization etc., preferably by recrystallization. Recrystallization may be carried out in solvent(s) or mixture of solvents, selected from the group comprising of ketones e.g. acetone, methyl ethyl ketone, cyclohexanone, 2-propanone, 4-methly-2 pentanone and the like; esters e.g. methyl acetate and ethyl acetate; nitriles e.g. acetonitrile and propionitrile; ethers e.g. diethyl ether, diisopropylether, dioxane, 1,2-dimethoxyethane, tetrahydrofuran and the like; preferred being ethers and the most preferred being diisopropylether.

The recrystallized 1-(3-hydroxy phenyl)ethyl-(N,N'-dimethyl)amine, compound of formula II, wherein $R^3$, $R^4$ and $R^5$ are methyl, of the present invention has a characteristic melting range of about 85 to 86° C.

More specifically, the 1-(3-hydroxy phenyl)alkyl-(N-mono/dialkyl)amine is 1-(3-hydroxyphenyl)ethyl-(N,N'-dimethyl)amine of the formula II, an intermediate of rivastigmine.

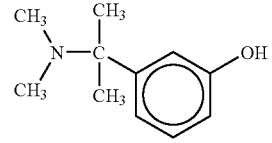

Formula II wherein $R^3$, $R^4$, and $R^5$ are methyl

The process of the present invention for example involves reacting 3-[1-(dimethylamino)ethyl]phenol with N-ethyl-N-methyl-4-nitrophenyl carbamate in the presence of potassium carbonate and dimethyl sulfoxide at a temperature ranging from about 80° C. to about 120° C. for about 30 to 40 hours, to form racemate of ethylmethylcarbamic acid 3-[1-(dimethylamino)ethyl]phenyl ester in the free base form. This racemate is then resolved to obtain the (S)-ethylmethylcarbamic acid 3-[1-(dimethylamino)ethyl]phenyl ester. The preferred method of resolution of the (S)-isomer from the racemate involves dissolving a mixture of the free base of the racemate and (+)-di-O, O'-p-toluoyl tartaric acid monohydrate in a 2:1 mixture of methanol: water by heating, collecting the precipitate on cooling by filtration, crystallizing the precipitate from a 2:1 mixture of ethanol:water, and obtaining the substantially pure (S)-isomer by partitioning it between 1N sodium hydroxide and a suitable organic solvent. The base may further be converted to its pharmaceutically acceptable acid addition salts, such as L(+)-tartrate salt.

The examples that follow do not limit the scope of the present invention and are included as illustrations.

EXAMPLE-1 a) Preparation of 3-(1-dimethylamino ethyl)phenol

Experimental Procedure

To the solution of 50% sulfuric acid in water (400.0 ml), was added at 10° to 15° C. temperature, DL-methionine (124.9 gm, 0.837 moles) and stirred for 15 minutes. To this solution, was added [1-(3-methoxyphenyl)ethyl]dimethylamine (100.0 gm, 0.553 moles) at 10° to 15° C. temperature within 2 hours and stirred for 30 minutes. Reaction mixture was then heated to 110° to 120° C. temperature for 28 hours.

The reaction mixture was diluted with water, basified to pH 8.5 to 9.0 using ammonia solution and extracted with dichloromethane. Organic extract was then washed with water, charcoalized and concentrated. Hexane was then added to the residue and crude product filtered.

b) Purification

Crude product was recrystallized from diisopropylether to give pure [1-(3-hydroxyphenyl)ethyl]dimethylamine (55.0 gm, 60% yield, Purity->99%) melting range: 85 to 86° C. temperature)

EXAMPLE-2

Preparation of N-ethyl-N-methyl-4-nitrophenyl carbamate

To the cooled solution (8-10° C.) of 50 gm (0.85 moles) N-ethyl-N-methylamine hydriiodide salt in 325 ml water, was added a solution of 75 gm (0.90 moles) Sodium bicarbonate in 1.0 L water maintained below 15° C. temperature. After addition was completed, 67 gm (0.8 moles) solid Sodium bicarbonate was added to the reaction mixture followed by a solution of 170 gm 4-Nitrophenyl chloroformate (0.85 moles) in 500 ml dichloromethane at 8-10° C. temperature. Reaction mixture was then warmed to 25-30° C. temperature and stirred for 3.0 hours. Aqueous work-up, followed by concentration of Dichloromethane gave crude N-ethyl-N-methyl-4-nitrophenyl carbamate, which was recrystallized from hot n-Hexane to give pure N-ethyl-N-methyl-4-nitrophenyl carbamate.

EXAMPLE-3 a) Preparation of (±)-ethylmethylcarbamic acid 3-[1-(dimethylamino)ethyl]phenyl ester (±-Rivastigmine) 3-(1-dimethylaminoethyl)phenol (200 gm, 1.21 moles), anhydrous potassium carbonate (252 gm, 1.515 moles), N-ethyl-N-methyl-4-nitrophenyl carbamate (340 gm, 1.82 moles) and dimethylsulfoxide (1 liter) are mixed and heated at a temperature of about 90° to about 110° C., under nitrogen atmosphere, for 3540 hours. The reaction mixture is cooled gradually to room temperature and filtered. The filtered solution is quenched in ice-water mixture and extracted with ethyl acetate to furnish racemic Rivastigmine.

b) Resolution of Rivastigmine Base

To the solution of 200 gm (0.8 moles) racemic Rivastigmine base in 2.0 L Methanol:water (2:1), was added 322.0 gm (0.8 moles) (+)-di-p-toluoyl tartaric acid monohydrate and resulting slurry was heated to 60-65° C. for 30 minutes to get clear solution. After cooling to 0-5° C., precipitated solid was filtered, dried at 50-55° C. and recrystallized 4 times from minimum volumes of Methanol:water (2:1) to get optically pure di-p-toluoyl tartrate salt of (S)-enantiomer of Rivastigmine. (Specific optical rotation=80-81.5°, c=5 in Methanol)

The above prepared salt was added in portions to a mixture of 1 N NaOH solution and n-hexane at 0-5° C. temperature, stirred for 30 minutes, and organic phase was separated. Organic phase was then washed twice with water and concentrated completely to get optically pure (S)-Enantiomer of Rivastigmine. (Specific optical rotation=−32°, c=5 in Methanol)

We claim:

1. A process for the preparation of (S)-isomer of compound of formula I,

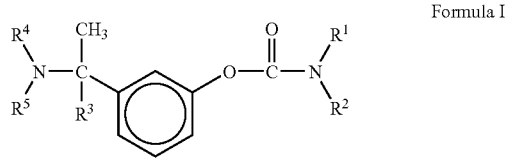

Formula I wherein $R^1$ is hydrogen, linear, branched or cyclic lower alkyl, cyclohexyl, allyl, propargyl or benzyl; $R^2$ is hydrogen, methyl, ethyl or propyl; or $R^1$ and $R^2$ together with the nitrogen to which they are attached form a cyclic moiety of three to eight-membered ring, with or without a hetero atom like nitrogen or oxygen; $R^3$ is hydrogen or lower alkyl; $R^4$ and $R^5$ are the same or different and each is a lower alkyl;

comprising reacting compound of formula II,

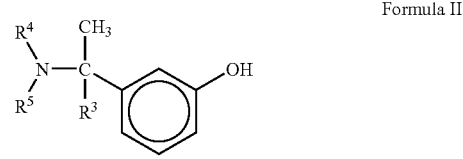

Formula II wherein $R^3$, $R^4$ and $R^5$ are as defined above, with compound of formula III,

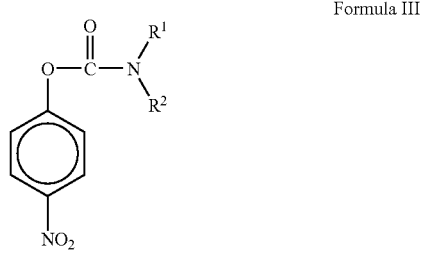

Formula III wherein $R^1$ and $R^2$ are as defined above,
in the presence of a base,
and further resolving the compound of formula I to obtain (S)-isomer of compound of formula I, substantially free of R-isomer.

2. A process as claimed in claim 1, wherein the base is selected from a group comprising alkali and alkaline earth metal oxides or hydroxides or carbonates, and secondary or tertiary amine bases.

3. A process as claimed in claim 2 wherein the base is an alkali carbonate.

4. A process as claimed in claim 3 where the base is potassium carbonate.

5. A process as claimed in claim 1 wherein the mole ratio of base with respect to compound of formula II, is in the range of about 1 mole to about 2 moles.

6. A process as claimed in claim 1, wherein the reaction is carried out using an organic solvent(s) having a boiling point greater than 60° C.

7. A process as claimed in claim 6 wherein the solvent is selected from the group comprising amides, ethers, polyethylene glycols of molecular weight 200 to 10,000, sulfoxides, and sulphones.

8. A process as claimed in claim 1, wherein the reaction is carried out at a temperature ranging from about 80° C. to about 110° C.

9. A process for the preparation of compound of formula II

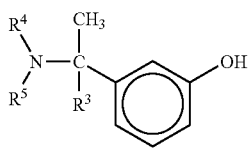

Formula II wherein $R^3$ is hydrogen or lower alkyl; $R^4$ and $R^5$ are the same or different and each is a lower alkyl; comprising dealkylating compound of formula IV,

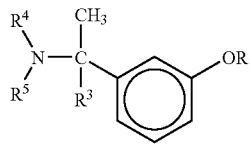

Formula IV wherein R is methyl, ethyl or benzyl, $R^3$, $R^4$ and $R^5$ are as defined above,
said dealkylation comprising reaction of compound of formula IV with a mixture of thioether and mineral acid.

10. A process as claimed in claim 9 wherein the compound of formula II is 1-(3-hydroxy phenyl)ethyl-(N,N'-dimethyl)amine.

11. A process as claimed in claim 9 wherein R is methyl.

12. A process as claimed in claim 9 wherein the thioether is methionine.

13. A process as claimed in claim 9 wherein the mineral acid is sulfuric acid.

14. A process as claimed in claim 13 wherein the concentration of sulfuric acid used is about 20% to 100%.

15. A process as claimed in claim 9 wherein the dealkylation is carried out at a temperature ranging from ambient to about 150° C.

16. A process as claimed in claim 9 wherein the molar ratio of methionine to compound of formula II ranges from about 0.5:1 to 3.0:1.

17. A process as claimed in claim 9 wherein the compound of formula II is optionally re-crystallized from ether.

18. A process as claimed in claim 17 wherein the ether is diisopropylether.

19. A process as claimed in claim 17 wherein the recrystallised compound of formula II wherein $R^3$, $R^4$ and $R^5$ are methyl is characterized by a melting range of about 85 to 86° C.

20. A process for the preparation of (S)-isomer of compound of formula I,

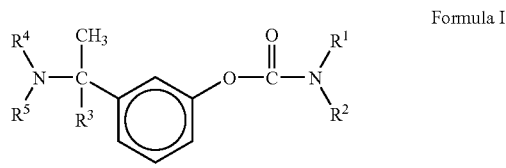

Formula I wherein $R^1$ is hydrogen, linear, branched or cyclic lower alkyl, cyclohexyl, allyl, propargyl or benzyl; $R^2$ is hydrogen, methyl, ethyl or propyl; or $R^1$ and $R^2$ together with the nitrogen to which they are attached form a cyclic moiety of three to eight-membered ring, with or without a hetero atom like nitrogen or oxygen; $R^3$ is hydrogen or lower alkyl; $R^4$ and $R^5$ are the same or different and each is a lower alkyl;
comprising
a) preparing compound of formula II

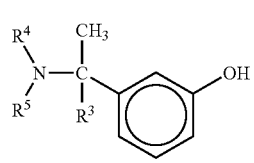

Formula II wherein $R^3$ is hydrogen or lower alkyl; $R^4$ and $R^5$ are the same or different and each is a lower alkyl;
by dealkylating compound of formula IV,

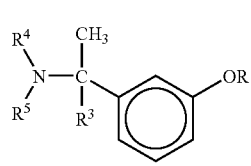

Formula IV wherein R is methyl, ethyl or benzyl, $R^1$, $R^2$ and $R^3$ are as defined above,
said dealkylation comprising reaction of compound of formula II with a mixture of thioether and mineral acid; and
b) reacting compound of formula II,

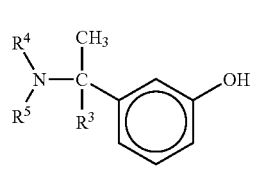

Formula II wherein $R^3$, $R^4$ and $R^5$ are as defined above,
with compound of formula III,

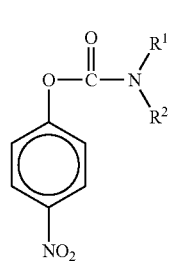

Formula III wherein $R^1$ and $R^2$ are as defined above,
in the presence of a base,
and further resolving the compound of formula I to obtain (S)-isomer of compound of formula I, substantially free of R-isomer.

* * * * *